[19] United States Patent
Victory

[11] 4,160,804
[45] Jul. 10, 1979

[54] DEVICE FOR ASSAYING GOLD AND OTHER METALS
[76] Inventor: Thomas J. Victory, 25167 Harcourt, Farmington, Mich. 48024
[21] Appl. No.: 930,416
[22] Filed: Aug. 2, 1978
[51] Int. Cl.² .................. B01L 9/00; G01N 31/00
[52] U.S. Cl. ................................................. 422/104
[58] Field of Search ............... 422/50, 68, 99, 104, 422/53; 220/4 B, 4 E

[56] References Cited
U.S. PATENT DOCUMENTS

| | | |
|---|---|---|
| 3,266,298 | 8/1966 | Whitehead et al. ............... 422/68 X |
| 3,525,264 | 8/1970 | Nieglos et al. .................... 422/104 X |
| 3,936,273 | 2/1976 | Powell ............................... 422/53 |

Primary Examiner—Arnold Turk
Attorney, Agent, or Firm—Harness, Dickey & Pierce

[57] ABSTRACT

Device facilitating the assay of gold or other metals by the method of comparative dissolution with acid. The device comprises a separable holder which contains a plurality of wire supports, each support having a gold wire of a different karat. The wire supports are replaceable simply by opening the holder and color coding is used to insure accurate location of the wires. The holder may also retain a file or tester for other metals such as silver.

7 Claims, 4 Drawing Figures

1

DEVICE FOR ASSAYING GOLD AND OTHER METALS

BACKGROUND OF THE INVENTION

1. Field of the Invention

The invention relates to the method of assaying of gold or other metals which uses a smooth black stone such as an Arkansas stone on which markings are applied. In particular, the invention relates to the means for holding the gold needles which are used in conjunction with this method.

2. Description of the Prior Art

In the known assaying method, a gold needle of known karat is first rubbed on the stone to create a streak. An unnoticeable part to the piece to be tested is used to make a mark next to the first mark. A streak of acid of known strength is then drawn across the two gold streaks, and observed to see which mark burns away first. This mark is of the lower karat so that if the mark of unknown karat burns away first, another needle of lower known carat may be selected and the test rerun until it is determined that the piece being tested is between two known carats. A prior art device for holding the test needles comprises a ring carrying a group of independently movable needle supports, each support comprising a tapered copper member to the outer end of which the gold needle of known carat is silver soldered. A problem with this conventional needle holding device is that the assaying equipment is usually kept in a closed box together with the testing stone and acid containers, and the acid fumes have a tendency to break down the silver soldered connections. The gold needles are thus apt to break off from the copper supports. If even one needle is lost, the entire tool and assaying kit becomes useless for its intended purpose.

BRIEF SUMMARY OF THE INVENTION

It is an object of the present invention to provide a novel and improved device for assaying gold and other metals which overcomes the above-described disadvantage of the known gold needle holder, and avoids the likelihood of loosening or dislodgement of the gold needles from their supports, thus insuring continued usefulness of the device.

It is a further object to provide an improved construction of this character which permits quick and easy replacement of gold needles which are worn or otherwise unusable, and insures proper location of the needles at all times.

It is another object to provide an improved assaying device of this character which is handy and compact, sturdy and reliable in use, economical to construct and is useful for various purposes allied to gold assaying.

Briefly, the gold assaying device of this invention comprises a clam shell type of holder having facing halves mating at their peripheral edges, a plurality of radially extending apertured portions formed by said mating edges, a plurality of needle supports, each support having a head within said peripheral edges and a narrower body portion extending through one of said apertured portions, a bore in each support holding a test needle, the needles in said supports being of different known karats, and indicia means on said holder identifying said known karats.

DESCRIPTION OF THE PREFERRED EMBODIMENT

Figure 1:
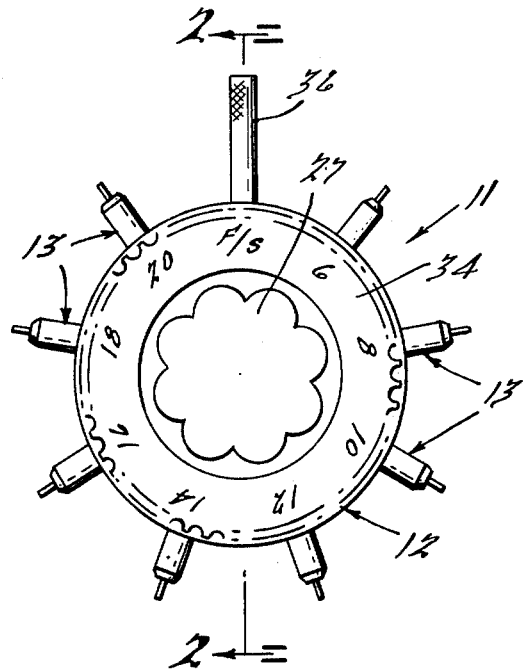
FIG. 1 is a side elevational view of the device of this invention shown with a set of gold needles and a file.

The device is generally indicated at 11 and comprises a holder generally indicated at 12 and a plurality of test wire supports generally indicated at 13. Holder 12 is of circular shape and has a separable clam shell type of construction, with halves 14 and 15 having mating peripheral edges 16 and 17 respectively. A circular wall 18 is formed inwardly of edges 16, 17 by mating portions of halves 14 and 15, forming an annular space 19 outwardly of wall 18. A central interior hub 21 is formed on holder half 14 and a hub 22 on half 15, these hubs extending toward each other and interfitting as indicated at 23. A space 24 is formed between wall 18 and hubs 21 and 22.

A screw fastener 25 extends through hubs 21 and 22 and has a nut 26 to hold the halves 14 and 15 together. A decorative decal 27 suitably conceals nut 26. The side surfaces of holder halves 14 and 15 are preferably of slightly convex shape to facilitate handling of the device.

Figure 4:
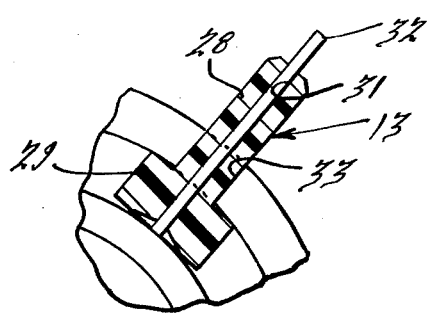
FIG. 4 is an enlarged fragmentary view taken in the area marked 4 of FIG. 3 and showing the construction of one of the test wire supports.

Each wire support 13 comprises a body portion 28 of tubular shape (FIG. 4) and an enlarged head 29. A central bore 31 is formed in each support and carries a test needle 32. This needle may, for example, be gold of a known karat, such as 6 karat, 8 karat, etc. up to 20 karats.

Figure 2:
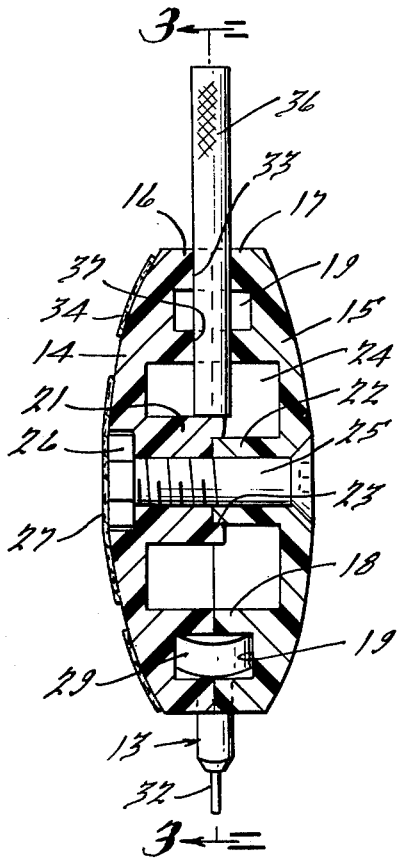
FIG. 2 is a cross-sectional view in elevation taken along the line 2—2 of FIG. 1 and showing the interior construction of the clam shell type holder.
Figure 3:
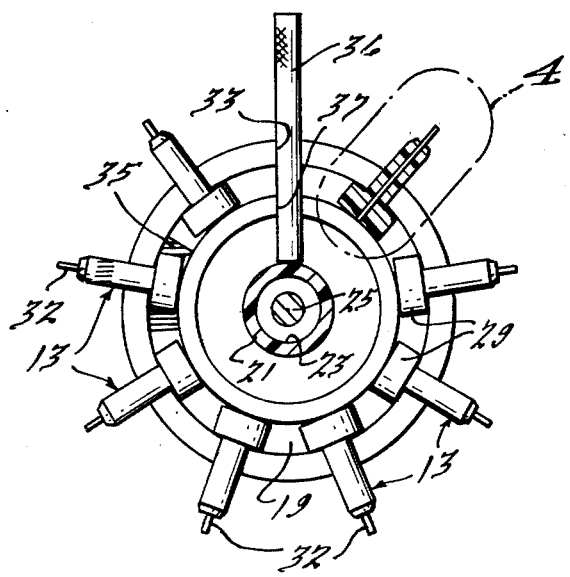
FIG. 3 is a partially sectioned view taken along the line 3—3 of FIG. 2 and illustrating the manner in which the support heads are captured by the holder and the file supported thereby.

A plurality of radial apertured portions 33 are formed in the peripheral edges 16 and 17 of holder halves 14 and 15, these apertured portions being circumferentially spaced around holder 12. Body portions 28 of supports 13 are disposed in these apertured portions with the supports extending outwardly so as to expose needles 32. Heads 29 of supports 13 are disposed in space 19 and held against radial movement by wall 18 and edges 16 and 17 as seen in FIGS. 2 and 3.

In the illustrated embodiment of the invention, eight wire testing needles are shown in eight supports 13. These range from 6 karats to 20 karats. An annular indicia decal 34 is provided on the side of holder half 14 surrounding decal 27. Decal 34 has imprinted thereon numerals designating the karats of the various wire needles. Additionally, each wire needle support 13 is of a different color and corresponding colors are imprinted in space 19 adjacent the apertured portions for those supports. For example, the support 13 for wire 32 having 18 karats could be blue and the area marked 35 in FIG. 3 could be colored blue also.

A file 36 is shown in the illustrated embodiment of the invention as occupying one of the apertured portions 33. An additional apertured portion 37 is formed in alignment with that aperture 33 in wall 18 as shown in FIGS. 2 and 3, so that the inner end of file 36 may be supported by hub 21. The indicia adjacent file 36 is "F/S" to indicate that instead of a file a silver testing wire in appropriate support 13 could be mounted at that location. In such a case, the presence of apertured portion 37 would not hinder the proper mounting of such a support.

In operation of device 11, once the parts are assembled as shown, it is merely necessary to mark the stone with the device being tested and then form a mark next to it with a wire 32 having a karat closest to that which is thought to be the proper karat. The acid test will show which mark has a lower karat, and the test may be repeated as described above until the karat of the piece being tested in bracketed by two known karats, for example, 14 karats and 16 karats. It will then be known that the test piece has a karat value somewhere between those two karats.

Since support of the wire test needles does not depend on silver solder, it is permissible to store device 11 in a box with the acid and stone without concern about loosening or dislodgement of the needles. Should it be necessary to replace one of the wire needles, it is merely required to remove screw 25 so as to separate the holder halves and remove and replace the proper support 13. The color coding will facilitate replacement and assure the proper location of the wires at all times.

While the above description constitutes the preferred embodiment of the invention, it will be appreciated that the invention is susceptible to modification, variation and change without departing from the proper scope of fair meaning of the accompanying claims.

I claim:

1. A gold assaying device comprising a clam shell type of holder having facing halves mating at their peripheral edges, a plurality of radially extending apertured portions formed by said mating edges, a plurality of needle supports, each support having a head within said peripheral edges and a body portion extending from one of said apertured portions, a bore in each support holding a test needle, the needles in said supports being gold of different known karats, and indicia means on said holder identifying said known karats.

2. The combination according to claim 1, said halves being circular, and central screw fastening means holding said halves together.

3. The combination according to claim 1 or 2, the heads of said supports being enlarged and disposed in an annular recess formed inwardly of said peripheral edges, and a wall formed by said halves radially inwardly from said recess, whereby said heads are prevented from inward radial movement.

4. The combination according to claim 1 or 2, further provided with a file mounted in and extending from one of said apertured portions, and a central portion on one of said mating halves limiting inward movement of said file.

5. The combination according to claim 1 or 2, said indicia comprising numerals on one side of said holder adjacent said apertured portions.

6. The combination according to claim 5, said indicia further comprising different colors on said supports, and corresponding colors on the interior of at least one of said holder halves adjacent said apertured portions.

7. The combination according to claim 1, said holder halves being circular, central hubs on said halves extending toward and interfitting with each other, an annular recess surrounding said hubs, and a wall surrounding said recess, said support heads being disposed in a second annular recess between said wall and said mating peripheral edges.

* * * * *